(12) United States Patent
Ren et al.

(10) Patent No.: US 12,257,079 B2
(45) Date of Patent: Mar. 25, 2025

(54) INTRAOCULAR PRESSURE SENSOR

(71) Applicant: MINGCHE BIOTECHNOLOGY CO., LTD, Suzhou (CN)

(72) Inventors: Dongni Ren, Suzhou (CN); Fule Wang, Shanghai (CN); Kemin Wang, Shanghai (CN); Ruixue Yin, Shanghai (CN); Heming Wei, Shanghai (CN); Hongbo Zhang, Shanghai (CN)

(73) Assignee: MINGCHE BIOTECHNOLOGY CO., LTD, Suzhou (CN)

( * ) Notice: Subject to any disclaimer, the term of this patent is extended or adjusted under 35 U.S.C. 154(b) by 9 days.

(21) Appl. No.: 17/971,060

(22) Filed: Oct. 21, 2022

(65) Prior Publication Data

US 2023/0337983 A1 Oct. 26, 2023

(30) Foreign Application Priority Data

Apr. 24, 2022 (CN) .......................... 202210432869.8

(51) Int. Cl.
*A61B 5/00* (2006.01)
*A61B 3/16* (2006.01)

(52) U.S. Cl.
CPC .............. *A61B 5/6847* (2013.01); *A61B 3/16* (2013.01); *A61B 2562/168* (2013.01)

(58) Field of Classification Search
CPC ... A61B 3/16; A61B 5/6847; A61B 2562/168; A61B 2562/0247; A61B 2562/0266; A61F 2/1654
USPC ...................................................... 623/6.31
See application file for complete search history.

(56) References Cited

U.S. PATENT DOCUMENTS

| 5,343,861 A * | 9/1994 | Herman .................. A61B 46/10 206/363 |
| 10,687,704 B2 | 6/2020 | Hastings et al. |
| 2004/0254438 A1 | 12/2004 | Chuck et al. |
| 2012/0302861 A1 | 11/2012 | Marshall et al. |
| 2013/0150777 A1 * | 6/2013 | Bohm .................. A61F 9/00781 604/9 |

(Continued)

FOREIGN PATENT DOCUMENTS

| CN | 107432733 A | 12/2017 |
| CN | 108634929 A | 10/2018 |

(Continued)

*Primary Examiner* — Benjamin S Melhus
*Assistant Examiner* — Raymond P Dulman
(74) *Attorney, Agent, or Firm* — ANOVA LAW GROUP, PLLC

(57) ABSTRACT

An intraocular pressure (IOP) includes a transmission film component, which is in direct contact with intraocular aqueous humor and configured to sense pressure fluctuations in the intraocular aqueous humor; a reflective film component set on an inner side of the transmission film component; and an adhesion layer component set on an inner layer of the reflective film component and configured to connect to an attachment device. An enclosed space formed by the reflective film component and the transmission film component constitutes a resonance chamber, which is filled with a filling medium. When a pressure in the intraocular aqueous humor is changed, the transmission film component is deformed, resulting in a change in a near-infrared (NIR) spectrum reflected by the reflective film component; the IOP is detected according to the change of the NIR spectrum.

12 Claims, 7 Drawing Sheets

(56) References Cited

U.S. PATENT DOCUMENTS

| | | | |
|---|---|---|---|
| 2016/0007851 A1* | 1/2016 | Araci | A61B 8/0841 |
| | | | 600/403 |
| 2017/0127941 A1 | 5/2017 | Ostermeier et al. | |
| 2017/0209045 A1 | 7/2017 | Choo et al. | |
| 2017/0251921 A1* | 9/2017 | Phan | A61B 3/16 |
| 2019/0380578 A1* | 12/2019 | Naber | H05K 1/0393 |
| 2021/0353145 A1* | 11/2021 | Kamthan | A61B 1/015 |

FOREIGN PATENT DOCUMENTS

| | | | | |
|---|---|---|---|---|
| CN | 113795188 A | 12/2021 | | |
| WO | 2012137067 A2 | 10/2012 | | |
| WO | 2013059195 A1 | 4/2013 | | |
| WO | 2017137911 A1 | 8/2017 | | |
| WO | WO-2018090330 A1 * | 5/2018 | | A61B 3/16 |
| WO | WO-2020210322 A1 * | 10/2020 | | A61B 3/16 |
| WO | WO-2020232015 A1 * | 11/2020 | | A61B 3/16 |

\* cited by examiner

INTRAOCULAR PRESSURE SENSOR

CROSS-REFERENCE TO RELATED APPLICATION

This application claims priority to Chinese Patent Application No. 202210432869.8, filed on Apr. 24, 2022, the content of all of which is incorporated herein by reference.

TECHNICAL FIELD

The present disclosure relates to the technical field of medical devices, in particular to an intraocular pressure (IOP) sensor.

BACKGROUND

As the first irreversible blindness disease in the world, glaucoma seriously affects people's quality of life. Intraocular pressure is always an important indicator for glaucoma condition, which is of vital importance to the diagnosis and postoperative observation by doctors.

At present, the measurement of IOP is mainly indirect measurement, which is used to measure corneal deformation mainly by utilizing various sensing principles, such as Imbert-Fick principle, electromagnetic induction probe rebound principle and PASCAL principle and then obtain the value of IOP by utilizing the relationship between corneal deformation and IOP. A comparative analysis on the currently commonly used IOP detection equipment is hereby made.

In 1954, Goldmann, an American, designed the Goldmann applanation tonometer (GAT). At present, GAT is regarded as the tonometer with the highest measurement accuracy and is the internationally recognized "gold standard" for IOP measurement, whose measurement results often serve as a standard for clinically measuring the accuracy of other tonometers. In order to avoid the decrease of IOP caused by indentation, measure only once and record the results. Although the measurement of GAT is accurate, it cannot be widely used in clinical practice due to the need for topical anesthesia, the need for patients to have certain cooperation ability, and the high technical requirements for examiners.

At present, ICare rebound tonometer (RBT) is a popular handheld tonometer in the market, which is newly developed based on the theory of inductive rebound proposed by Antti Kontiola. For each measurement, patients need to adjust the probe to the appropriate distance from the cornea, take the correct sitting position, look ahead and fully relax. The accuracy of RBT measurement results has great relevance to the proficiency of the operator, operation method and the location where the single-use probe hits the cornea.

NCT is one of the most widely used tonometers in clinical practice in China, which, together with GAT, falls into the scope of applanation tonometers. NCT is suitable for large-scale census and outpatient owing to simple operation, good repeatability for repeated measurements and easy acceptance by patients. However, it's not suitable for the measurement of IOP in patients with high astigmatism, corneal opacity and poor fixation, and patients having received corneal transplantation. In addition, studies have shown that the stability of NCT in the measurement of high IOP area is low, and since NCT is a large bench device, patients can only be measured in sitting position. Therefore, NCT is not suitable for patients with mobility difficulties and elderly patients.

Triggerfish CLS is a contact-type IOP sensor. When IOP of human is changed, the corneal curvature will be changed, which is the physiological characteristic of human eye serving as the basis for the design of Triggerfish CLS. The biggest advantage of Triggerfish CLS is non-invasive continuous monitoring for simple, fast and convenient operation. However, it also has the significant disadvantage that it can only provide the relative change of IOP but not the absolute IOP, which causes inconvenience for the diagnosis of doctors. In addition, Triggerfish CLS has a certain impact on the field of view when being worn for the presence of built-in induction coil, chip, etc.

At present, the above products are commonly used tonometers in clinical practice, all of which have the disadvantages of incapability of continuous measurement or low measurement accuracy.

SUMMARY

The technical problem to be solved by the present disclosure is as follows: In order to solve the problem that tonometers in the prior art can be only used for single measurement or have low measurement accuracy, the present disclosure provides an IOP sensor intended to be implanted into the anterior chamber of eyes for continuous detection of IOP, with direct measurement method and high measurement accuracy, which solves the problem that tonometers in the prior art can be only used for single measurement, and improves the accuracy of measurement results.

The technical scheme adopted by the present disclosure to solve the technical problem is as follows. The IOP sensor includes a transmission film component, which is in direct contact with intraocular aqueous humor and configured to sense pressure fluctuations in the intraocular aqueous humor; a reflective film component set on an inner side of the transmission film component; and an adhesion layer component set on an inner layer of the reflective film component and configured to connect to an attachment device. An enclosed space formed by the reflective film component and the transmission film component constitutes a resonance chamber, which is filled with a filling medium. When a pressure in the intraocular aqueous humor is changed, the transmission film component is deformed, resulting in a change in a near-infrared (NIR) spectrum reflected by the reflective film component; the IOP is detected according to the change of the NIR spectrum.

In some embodiments, the transmission film component, the reflective film component and the adhesion layer component are made of light curing materials.

In some embodiments, the outer surface of the transmission film component has a surface plasmon structure.

In some embodiments, the surface plasmon structure is a lattice or boss structure.

In some embodiments, the reflective film component is provided with a total reflection structure.

In some embodiments, the total reflection structure is in pyramid array.

In some embodiments, the reflective film component is made of the material with high refractive index greater than 1.5.

In some embodiments, the material with high refractive index is doped with inorganic nanoparticles.

In some embodiments, the inorganic nanoparticles are selected from at least one of Ge, Bi, SiN and $SiO_2$.

In some embodiments, the filling medium is liquid or gas.

In some embodiments, the liquid is selected from any one of uncured light curing material (i.e., a light curing material that has not been cured) or glycerin; the gas is selected from any one of air, oxygen and inert gas.

In some embodiments, when the filling medium is not made of the uncured light curing material, the adhesion layer component is provided with a blocked drainage hole.

The present disclosure has the following beneficial effects: the IOP sensor provided by the present disclosure is simple in structure and convenient in operation, and has the ability of continuous non-invasive detection of IOP. The sensor is intended to be implanted into the anterior chamber of patients' eyes to directly measure the pressure of anterior aqueous humor by utilizing the principle of multibeam interference according to the change in pressure difference between the aqueous humor and the filling medium, which, on the one hand, reflects the real IOP of patients and improves the accuracy of measurement results, and on the other hand, enables patients to conduct self-detection at any time without the operation of doctors and solves the problem that tonometers in the prior art can be only used for single measurement, thus improving the comprehensive performance of the IOP sensor.

BRIEF DESCRIPTION OF DRAWINGS

The present disclosure is further explained in combination with the drawings and embodiments.

DETAILED DESCRIPTION

The present disclosure is hereby further described in detail. The embodiments described below are exemplary, which are intended to explain the present disclosure and cannot to be construed as limitations to the present disclosure. Based on the embodiments of the present disclosure, all other embodiments obtained by ordinary technicians in the field without creative work fall within the scope of protection of the present disclosure.

Figure 1:
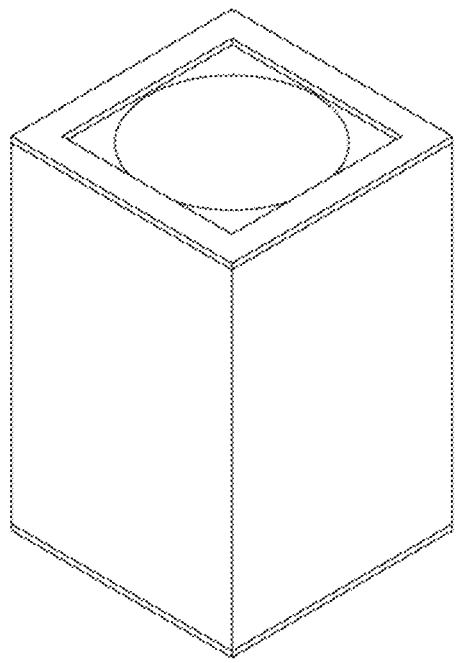
FIG. 1 is the structural diagram I of the IOP sensor in the present disclosure.
Figure 4:
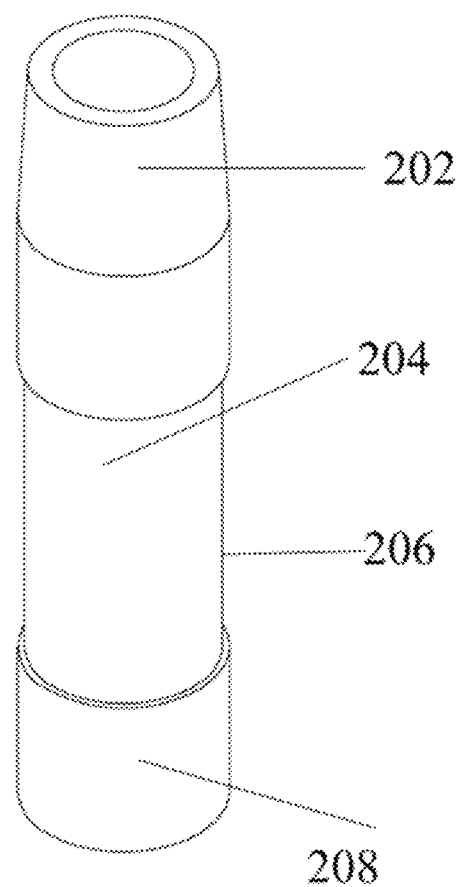
FIG. 4 is the structural diagram II of the IOP sensor in the present disclosure.

In order to solve the problem that tonometers in the prior art can be only used for single measurement or have low accuracy, the present disclosure provides an IOP sensor, as shown in FIGS. 1 and 4. The IOP sensor includes: a transmission film component 102, which is in direct contact with intraocular aqueous humor for sensing the pressure fluctuations of the intraocular aqueous humor and has a transmission film body on which a cladding layer can be arranged to increase transmissivity; a reflective film component 104, which is set on the inner side of the transmission film component 102 and has a reflective film body of either a printed layer mirror with strong reflectivity or a flat mirror with zero curvature corresponding to the shape of the transmission film component 102; and an adhesion layer component 106, which is set on the inner layer of the reflective film component 104 configured to connect to an attachment device that can be a medical device that performs a specific function, such as a drainage tube for the treatment of glaucoma. The enclosed space formed by the reflective film component 104 and the transmission film component 102 constitutes a resonance chamber 110, which is filled with a filling medium to form a certain pressure within the resonance chamber 110.

Figure 6:
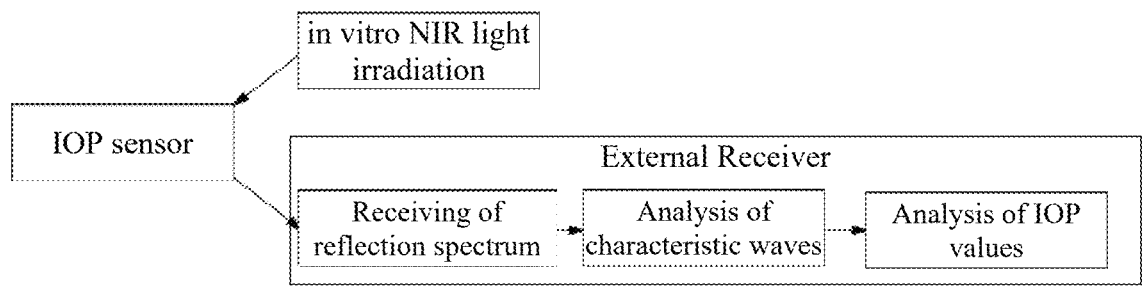
FIG. 6 is the detection process diagram of the IOP sensor in the present disclosure.

During use, the IOP sensor can be implanted into the anterior chamber of the patient's eye to make the transmission film component 102 come into contact with the aqueous humor in the eye, so that the intraocular aqueous humor and the filling medium are located on both sides of the transmission film component 102. When the pressure of the aqueous humor in the eye is changed, the pressure difference between the filling medium in the resonance chamber 110 and the aqueous humor in the eye will also be changed due to the constant pressure of the filling medium in the chamber, which causes deformation of the transmission film component 102, thus resulting in the change of the thickness of the resonance chamber 110, that is, the distance between the transmission film component 102 and the reflective film component 104 and the change of reflection spectrum. As shown in FIG. 6, when the sensor is irradiated with in vitro NIR light, the deformation of the transmission film component results in the change of the NIR spectrum as reflected by the reflective film component 104. The external receiver receives the reflection spectrum to analyze the characteristic wave and IOP value for the purpose of the detection of IOP according to the change of the NIR spectrum. The preferred wavelength range of the NIR light is 800 nm to 2000 nm for the present disclosure.

The transmission film component 102 constitutes the external profile of the IOP sensor, and the transmission film component 102, reflective film component 104 and adhesion layer component 106 are all of annular structure. The adhesion layer component 106 has an internal columnar cavity 108. The specific structure and size can be set according to demand.

The IOP sensor provided by the present disclosure is simple in structure and convenient in operation, and has the ability of continuous non-invasive detection of IOP. The sensor is intended to be implanted into the anterior chamber of the patient's eye to directly measure the pressure of anterior aqueous humor by utilizing the principle of multi-beam interference according to the change in pressure difference between aqueous humor and a filling medium, which, on the one hand, reflects the real IOP of patients and improves the accuracy of measurement results, and on the other hand, enables patients to conduct self-detection at any time without the operation of doctors and solves the problem that tonometers in the prior art can be only used for single measurement, thus improving the comprehensive performance of the IOP sensor.

Although the existing Triggerfish CLS can also be used for continuous monitoring of IOP, it cannot be implanted and may affect patients' field of view when being worn. Moreover, the IOP sensor is used for measuring IOP according to the change of corneal curvature with the change of the IOP, which cannot be used for direct measurement of IOP, with low accuracy of measurement results.

The IOP sensor provided by the present disclosure can be used not only for continuous measurement but also for direct measurement of IOP, which improves the accuracy of measurement results, thereby improving the comprehensive performance of the IOP sensor.

The IOP sensor provided by the present disclosure can be manufactured by such methods as light curing micro-nano printing, gas phase precipitation, mold forming, and two-photon printing, which is preferred for integrated printing molding for the present disclosure. The transmission film component 102, the reflective film component 104 and the adhesion layer component 106 are preferably made of light curing material, which can be any light curing material in the prior art suitable for implantation in the patient's eye, such as the material made by curing with light-cured resin, the material made by curing with light-cured resin and monomer, or the material made by curing with various light-cured resins.

In order to improve the sensitivity of detection, the external surface of the preferred transmission film component 102 is of surface plasmon structure for the present disclosure to increase the amplitude of reflected light.

The surface plasmon structure is a lattice or boss structure which can be nano-gold lattice formed by gold printing.

In order to ensure the detection effect, the diameter range of each dot in the lattice structure preferred for the present disclosure is 300 nm to 800 nm, and the lattice range corresponds to the position of the reflective film component 104.

In order to further improve the sensitivity of detection, the reflective film component 104 preferred for the present disclosure is designed with a total reflection structure to enhance the reflection ability, so as to improve the sensitivity of detection.

The total reflection structure preferred for the present disclosure is in pyramid array.

For the IOP sensor provided by the present disclosure, the refractive index of the reflective film component 104 can also be increased by choosing a material with high refractive index for it, so as to improve the sensitivity of detection. Specifically, the material with high refractive index for the present disclosure refers to the material whose refractive index is greater than 1.5.

In order to further improve the refractive index, the material doped with inorganic nanoparticles is preferred for the reflective film component 104 in the present disclosure, and the material doped with inorganic nanoparticles with high refractive index is more preferred. The inorganic nanoparticles can be selected from at least one of Ge, Bi, SiN and $SiO_2$.

The filling medium in the resonance chamber 110 in the present disclosure can be any liquid or gas that can exist stably in the resonance chamber 110 for the convenience of measuring the change of aqueous humor pressure in the eye.

When the filling medium is a liquid, the liquid may be selected from either an uncured light-curing material or glycerol; when the filling medium is a gas, the gas can be selected from any one of the air, oxygen and inert gas.

Specifically, the uncured light-curing material can be an uncured light-curing material for printing the overall structure of the IOP sensor, that is, a printed material.

Specifically, as a certain amount of fluid is needed to serve as the filling medium in the resonance chamber 110, a certain amount of printing material may be retained in the resonance chamber 110 in the printing process of the IOP sensor. The printing material is the uncured light curing material, which can directly serve as the filling medium.

Figure 10:
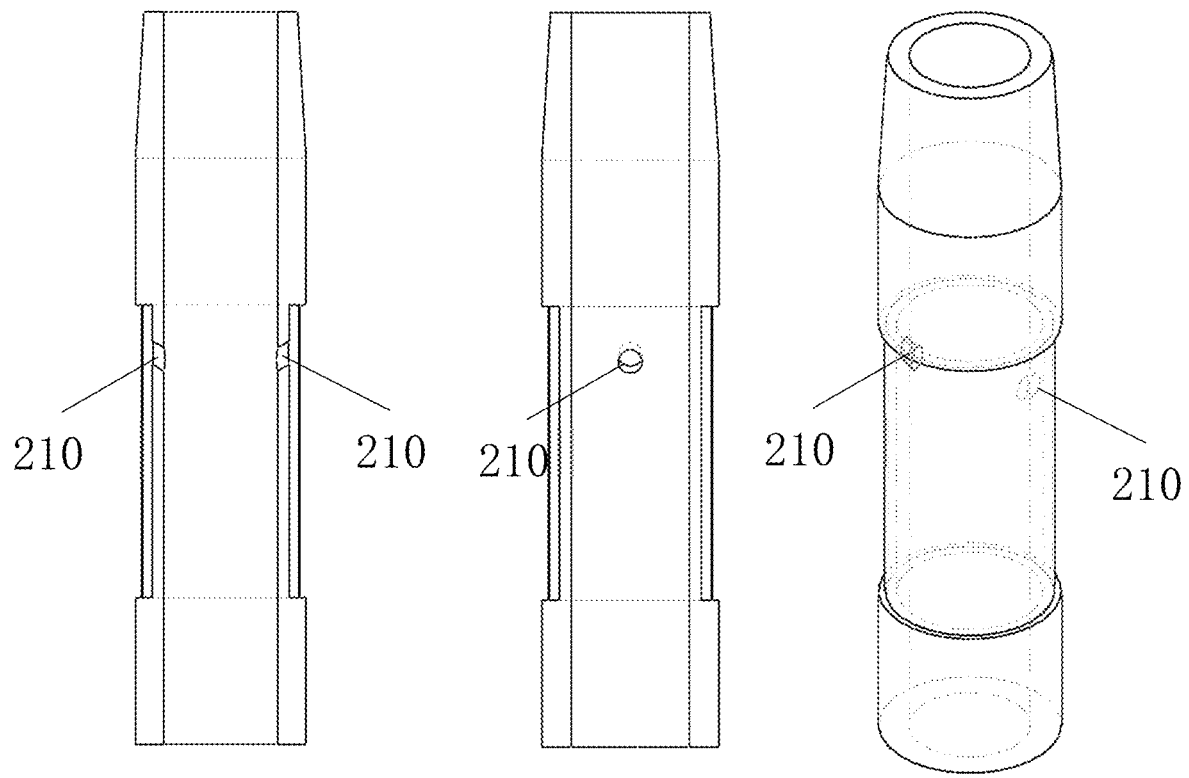
FIG. 10 illustrates structural diagrams of an IOP sensor containing a drainage hole in accordance with an embodiment of the present disclosure, including a front view, a side view, and a perspective view of the IOP sensor.

If a fluid other than the printing material, such as glycerin, air or inert gas, is selected as the filling medium, it is necessary to set a drainage hole (for example, drainage hole 210 as shown in FIG. 10) on the adhesion layer component 106 to be connected with the resonance chamber 110 in the manufacturing process of the IOP sensor for discharging the printing material retained in the resonance chamber 110 in printing process and for filling required filling medium into the resonance chamber 110. The diameter range of the drainage hole preferred for the present disclosure is 10 μm to 50 μm.

Besides, after filling the filling medium into the resonance chamber 110, it is also necessary to seal and block the drainage hole to have it disconnected with the resonance chamber 110. To be specific, the drainage hole can be blocked by making a cylinder matching the inner cavity of the adhesion layer component 106 and externally painted with a photosensitive adhesive to be inserted into the inner cavity 108 of the adhesion layer component 106 and fitted closely with the inner cavity 108 of the adhesion layer component 106 by aid of light. The cylinder inserted into the adhesion layer component 106 can be extended axially beyond the IOP sensor, while the extended part can be secured on the tissue.

The overall structure of the IOP sensor in the present disclosure can be of prism, cylinder and other geometric structure. One structure for the IOP sensor is as follows: the front segment 208 is cylindrical, with a diameter of 250 μm to 500 μm, a wall thickness of 50 μm to 100 μm, and a length of 250 μm to 1000 μm; the middle segment 204 is polyhedral or cylindrical, with the envelope of polyhedral edge 206 located in the external profile of the front segment 208 and spaced 2 μm to 20 μm apart; the end segment 202 is of round table structure with a certain gradient, whose large end is in contact with the middle segment 204, with a wall thickness of 50 μm to 100 μm, a height of 250 μm to 1000 μm, and a slope of 5° to 30°; the reflective film component 104 is polygonal with single feature or of a closed structure formed by feature polygons. Another structure for the IOP sensor is as follows: The IOP sensor has an external square cylinder structure and an internal cylindrical cavity. See the above descriptions for specific sizes.

The IOP sensor provided by the present disclosure is small in size and can be implanted into the eye through minimally invasive surgery with little damage to human body.

For embodiment, of the existing IOP sensors, EYEMATE is an implantable IOP sensor for in situ measurement. The sensor is equipped with a special integrated chip (MEMS-ASIC) and integrated with an antenna, an induction coil, etc., which can directly sense IOP through the pressure sensor and wirelessly transmit the IOP data. The sensor power supply powers the sensor under the principle of magnetic induction. The encapsulated EYEMATE has an inner diameter of 7 mm and outer diameters of 11.3 mm, 11.7 mm and 12.1 mm. ASIC has a thickness of 0.9 mm, or otherwise 0.5 mm around the microcoil. Its surface is in lenticular round shape for smoothly accommodating the curved sclera shape. The second-generation EYEMATE is structurally improved compared with the first-generation EYEMATE, with the size of 7.5×3.3 mm, the peripheral thickness of 0.9 mm, and the central thickness of 2.2 mm. Due to its large size, EYEMATE needs to be surgically implanted, which brings a certain risk of infection and inconvenience for replacement and maintenance if it's damaged.

Compared with the existing EYEMATE IOP sensor, the IOP sensor provided by the present disclosure is reduced in size by 1 to 2 orders of magnitude, which can be implanted into the eye by minimally invasive method to reduce the harm to human body.

In addition, the IOP sensor provided by the present disclosure can also be connected with a drainage device with the function of drainage of aqueous humor through the attachment device to make the IOP sensor highly scalable.

In order to make the above purposes, characteristics and advantages of the present disclosure more obvious and easily understandable, the specific embodiments of the present disclosure are explained in detail in combination with the drawings below.

Embodiment 1

Figure 2:
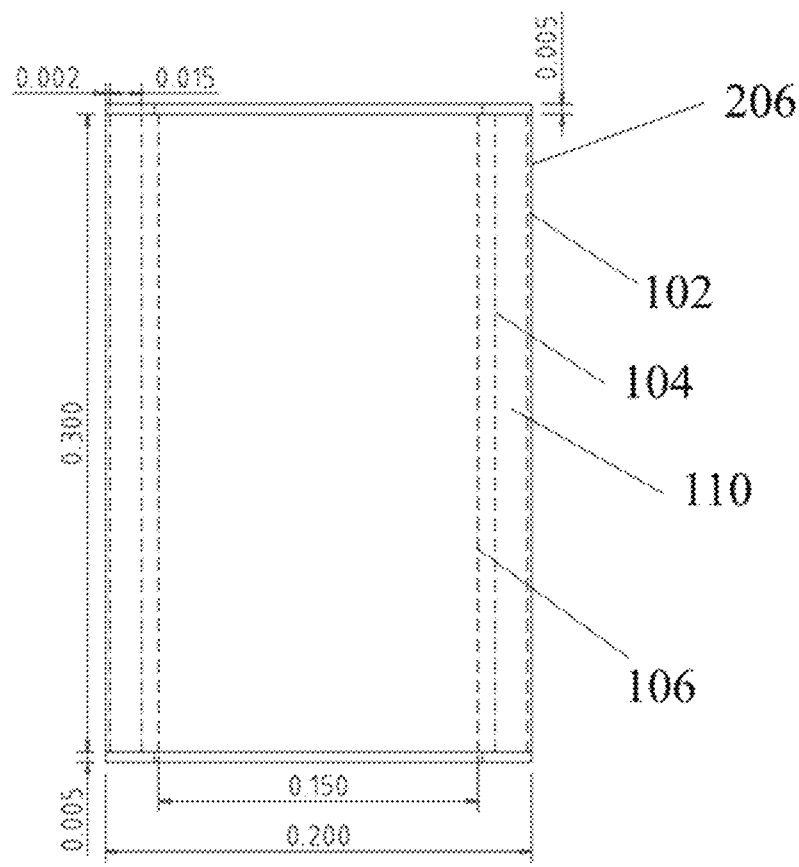
FIG. 2 is the size diagram I of the IOP sensor in Embodiment 1 of the present disclosure.
Figure 3:
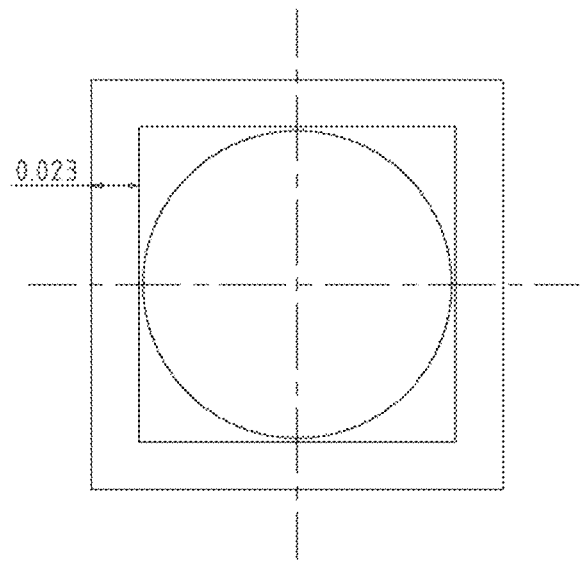
FIG. 3 is the size diagram II of the IOP sensor in Embodiment 1 of the present disclosure.

The embodiment provides an IOP sensor suitable for minimally invasive implantation into the anterior chamber of the patient's eye, as shown in FIG. 1. The IOP sensor has an overall shape of square column and internal shape of column. As shown in FIGS. 2 and 3, the IOP sensor has an appearance size of 0.2×0.2×0.31 mm, with the height of 0.31 mm composed of 0.005 mm for upper and lower parts of the resonance cavity cover respectively and 0.3 mm for the intermediate part of the effective detection region. In the embodiment, the IOP sensor has an inner round cavity diameter of 0.15 mm, which is also the diameter of the inner cavity of the adhesion layer component 106, whose size mainly depends on the size of the attachment device and can be adjusted as appropriate according to it. The IOP sensor has a film thickness of 0.002 mm, which is also the thickness of the transmission film component 102. The resonance chamber 110 has an inner cavity thickness of 0.015 mm, and the reflective film component 104 has a thickness of 0.008 mm. As thus, the transmission film component 102, the resonance chamber 110 and the reflective film component 104 have an overall thickness of 0.025 mm. As shown in FIG. 3, the cover has a thickness of 0.023 mm.

The IOP sensor in the embodiment is printed integrally by two-photon printing technology, and the filling medium in the resonance chamber 110 is printing material, with no need for drainage hole.

Embodiment 2

The embodiment provides an IOP sensor suitable for minimally invasive implantation into the anterior chamber of the patient's eye, as shown in FIG. 4. The TOP sensor has an overall appearance of cylinder, with an internal structure of round cylinder.

Figure 5:
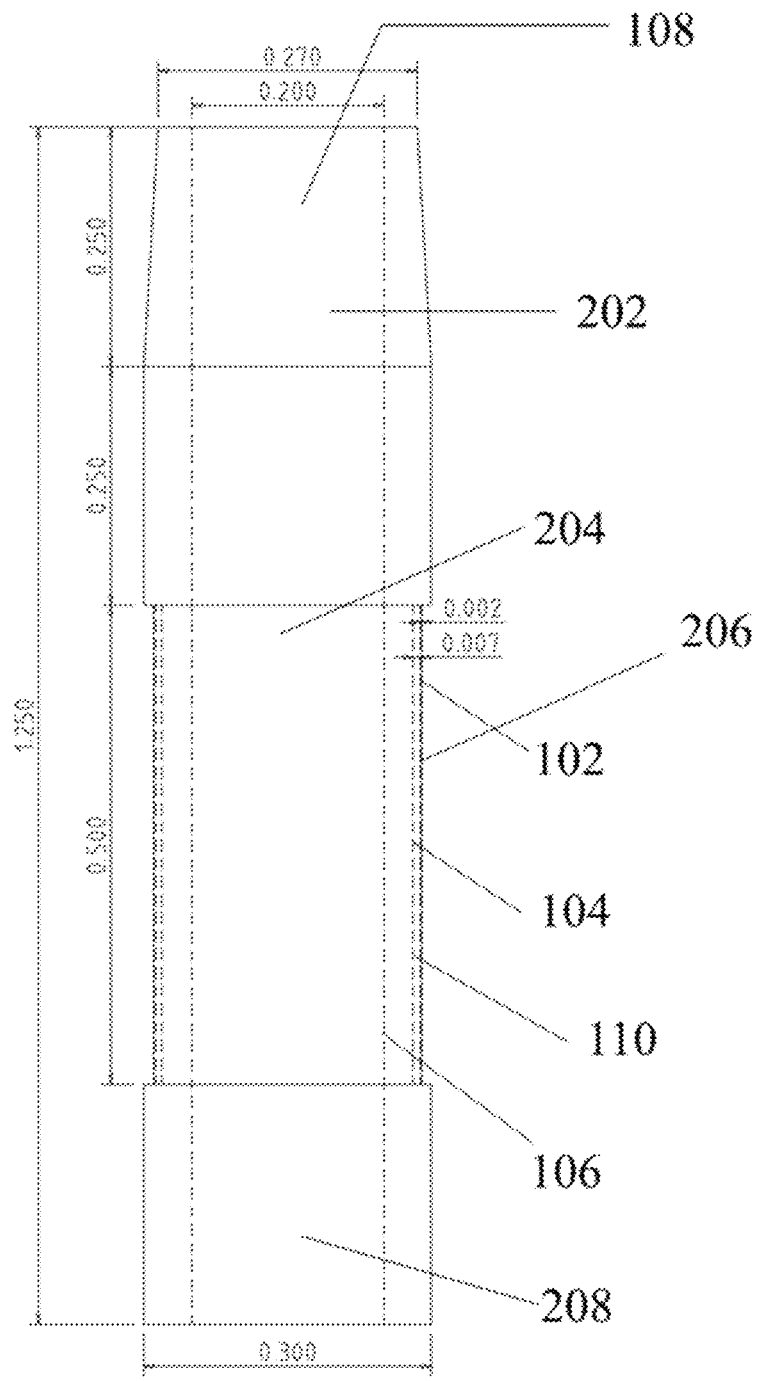
FIG. 5 is the size diagram of the IOP sensor in Embodiment 2 of the present disclosure.

As shown in FIG. 5, the IOP sensor has an overall height of 1.25 mm, an outer diameter of 0.3 mm and an inner diameter of 0.22 mm. The transmission film component 102 has a thickness of 0.002 mm, and the resonance chamber 110 has a thickness of 0.007 mm. The adhesion layer component 106 is provided with a drainage hole connected with the resonance chamber 110.

Detection Example

Figure 7:
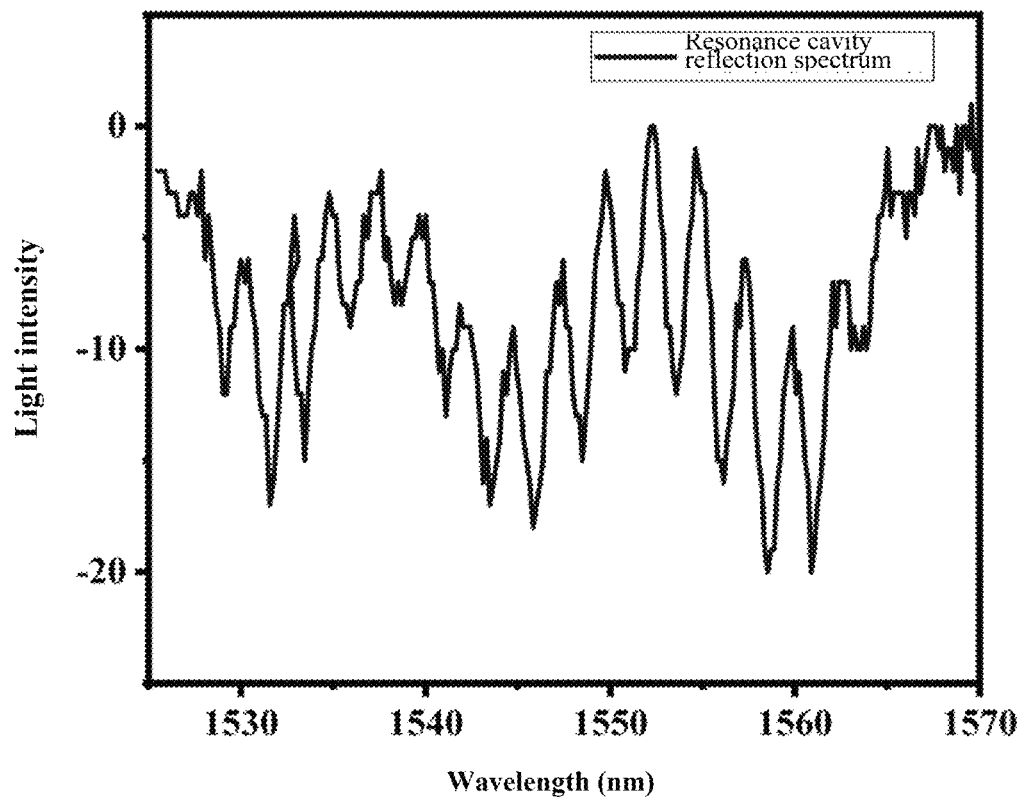
FIG. 7 is the detection spectrum obtained in the detection example of the present disclosure.
Figure 8:
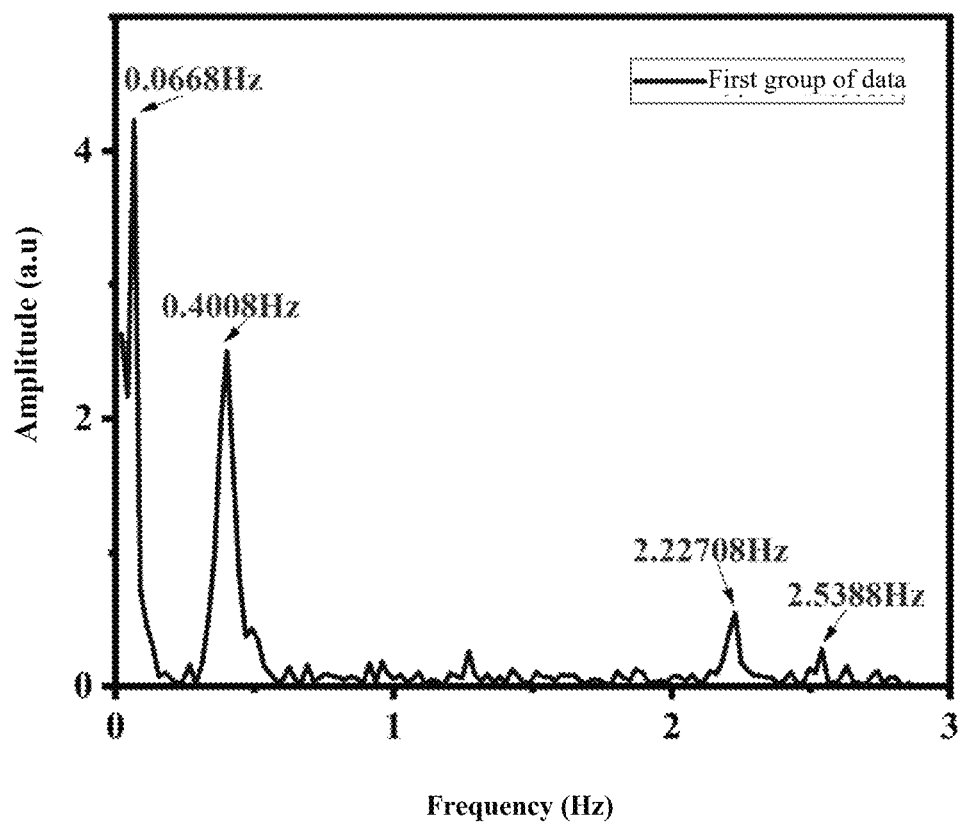
FIG. 8 is the characteristic wave of the detection spectrum in the detection example of the present disclosure.
Figure 9:
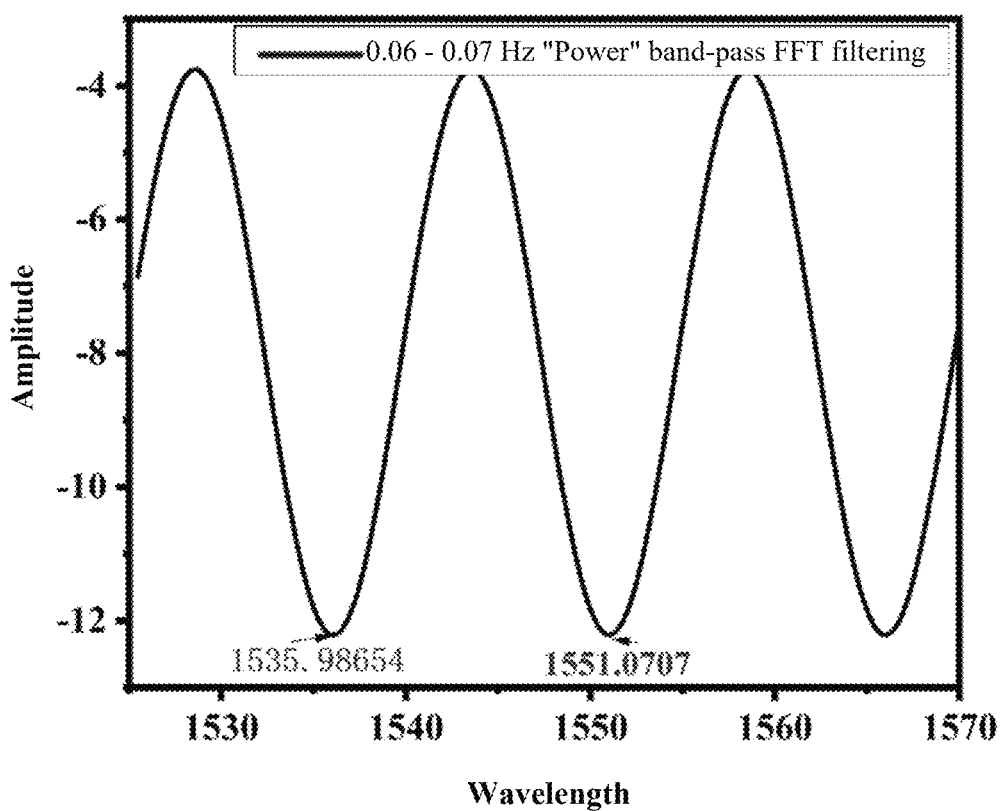
FIG. 9 is the characteristic spectrum of the detection spectrum in the detection example of the present disclosure.

In the detection example, the IOP sensor provided in Embodiment 1 is used for detection according to the detection method shown in FIG. 6. The detection spectrum shown in FIG. 7 contains the comprehensive spectrum of the resonance cavity thickness. The amount of characteristic waves is analyzed by fast Fourier transform to obtain the spectrum as shown in FIG. 8. The detection spectrum is subject to filtering processing according to analyzed characteristic waves to obtain the characteristic spectrum as shown in FIG. 9. The thickness of the resonance chamber 110 is calculated according to the characteristic spectrum, and the IOP is further calculated according to the thickness.

The specific calculation process of IOP is as follows:

According to the calculation formula of the cavity length (resonance cavity thickness) of Fabry-perot (F-P) Cavity: $fsr=\lambda^2/2\ nL$.

Wherein, fsr is the distance between two troughs; $\lambda$ is the mean wavelength between two troughs; n is the refractive index of the filling medium; and L is the thickness of the resonance cavity. The characteristic cavity thickness of the resonance cavity is calculated according to the spectral analysis results in FIG. 9. Under the pressure of aqueous humor in the glaucoma patient's eye, the transmission film component 102 is deformed to a certain degree, while the aqueous humor pressure changes proportionally with the decrease of the cavity thickness. On this basis, the patient's intraocular aqueous humor pressure (namely IOP) is obtained.

Inspired by the above ideal embodiments according to the present disclosure, the relevant staff can make various changes and modifications without deviating from the technical idea of the present disclosure based on the above descriptions. The technical scope of the present disclosure is not limited to the contents in the specification, and the technical scope must be determined according to the scope of the claims.

What is claimed is:

1. An intraocular pressure (IOP) sensor, comprising:
a transmission film component configured to be in direct contact with intraocular aqueous humor and sense pressure fluctuations of the intraocular aqueous humor;
a reflective film component set on an inner side of the transmission film component
a resonance chamber, which is an enclosed space formed by the reflective film component and the transmission film component, the resonance chamber being filled with filling medium;
an adhesion layer component set on an inner layer of the reflective film component and configured to connect to an attachment device;
wherein when a pressure in the intraocular aqueous humor is changed, the transmission film component is deformed, resulting in a change in a near-infrared (NIR) spectrum reflected by the reflective film component;
when the IOP sensor is irradiated with in vitro NIR light, the IOP is detected by an external receiver that receives the NIR spectrum reflected by the reflective film component and analyzes an IOP value according to the change of the NIR spectrum; and
wherein: an external profile of the IOP sensor, the transmission film component, the reflective film component, and the adhesion layer component are all of cylindrical annular structure, the transmission film component is sleeved on and wrapped around the cylindrical annular structure of the reflective film component, and the resonance chamber formed by the reflective film component and the transmission film component is annular;
a front segment of the IOP sensor is cylindrical, with a diameter of 250 μm to 500 μm, a wall thickness of 50 μm to 100 μm, and a length of 250 μm to 1000 μm;

a middle segment is polyhedral or cylindrical, with an envelope of polyhedral edge located in an external profile of the front segment and spaced 2 µm to 20 µm apart;

an end segment is of round table structure with a certain gradient, one end of the end segment is in contact with the middle segment, with a wall thickness of 50 µm to 100 µm, a height of 250 µm to 1000 µm, and a slope of 5° to 30°.

2. The IOP sensor according to claim 1, wherein the transmission film component, the reflective film component and the adhesion layer component are made of light curing materials.

3. The IOP sensor according to claim 2, wherein the reflective film component is made of a material with a refractive index greater than 1.5.

4. The IOP sensor according to claim 3, wherein the material is doped with inorganic nanoparticles.

5. The IOP sensor according to claim 4, wherein the inorganic nanoparticles are selected from at least one of Ge, Bi, SiN and SiO2.

6. The IOP sensor according to claim 2, wherein the filling medium is liquid or gas.

7. The IOP sensor according to claim 6, wherein the liquid is one of the light curing material that has not been cured or glycerin;

the gas is selected from one of air, oxygen and inert gas.

8. The IOP sensor according to claim 1, wherein the IOP sensor is printed integrally.

9. The IOP sensor according to claim 8, wherein a printing material of the IOP sensor is retained in the resonance chamber in a printing process of the IOP sensor and directly serve as a filling medium of the resonance chamber.

10. The IOP sensor according to claim 1, wherein the adhesion layer component of the IOP sensor has an internal cylindrical cavity.

11. The IOP sensor according to claim 1, wherein the filling medium is not made of a light curing material that has not been cured, and the adhesion layer component is provided with a drainage hole;

in a manufacturing process of the IOP sensor, the drainage hole is connected with the resonance chamber and configured to discharge a printing material retained in the resonance chamber in a printing process of manufacturing the IOP sensor, and received required filling medium into the resonance chamber; and after filling the filling medium into the resonance chamber, the drainage hole is sealed and disconnected with the resonance chamber.

12. An intraocular pressure (IOP) detection system, comprising:

an IOP sensor, comprising:
 a transmission film component configured to be in direct contact with intraocular aqueous humor and sense pressure fluctuations of the intraocular aqueous humor;
 a reflective film component set on an inner side of the transmission film component
 a resonance chamber, which is an enclosed space formed by the reflective film component and the transmission film component, the resonance chamber being filled with filling medium; and
 an adhesion layer component set on an inner layer of the reflective film component and configured to connect to an attachment device;
 wherein when a pressure in the intraocular aqueous humor is changed, the transmission film component is deformed, resulting in a change in a near-infrared (NIR) spectrum reflected by the reflective film component; and an external receiver configured to receive, when the IOP sensor is irradiated with in vitro NIR light, the NIR spectrum reflected by the reflective film component, analyze a characteristic wave to obtain an IOP value according to the change of the NIR spectrum, wherein: an external profile of the IOP sensor, the transmission film component, the reflective film component, and the adhesion layer component are all of cylindrical annular structure, the transmission film component is sleeved on and wrapped around the cylindrical annular structure of the reflective film component, and the resonance chamber formed by the reflective film component and the transmission film component is annular.

* * * * *